US00PP09689P

United States Patent [19]

Ilsink

[11] Patent Number: Plant 9,689

[45] Date of Patent: Nov. 12, 1996

[54] FLORIBUNDA ROSE PLANT VARIETY NAMED 'INTERPUR'

[75] Inventor: G. P. Ilsink, Doorn, Netherlands

[73] Assignee: DeVor Nurseries, Inc., Watsonville, Calif.

[21] Appl. No.: 597,901

[22] Filed: Feb. 7, 1996

[51] Int. Cl.[6] ..... A01H 5/00

[52] U.S. Cl. ..... Plt./27

[58] Field of Search ..... Plt./22, 26, 27

*Primary Examiner*—Howard J. Locker

*Attorney, Agent, or Firm*—Christie, Parker & Hale, LLP

[57] ABSTRACT

A new variety of floribunda rose plant producing purple-pink flowers.

1 Drawing Sheet

SUMMARY OF THE INVENTION

The present invention relates to a new and distinct variety of rose of the floribunda rose class which was originated by my crossing as seed and pollen parents two unnamed, unpatented, undistributed, proprietary seedlings of my creation. The varietal denomination of this new rose is 'Interpur'.

Among the novel characeristics possessed by this new variety which distinguishes it from its parents are its ability to produce commercially desirable sprays of attractive purple-pink flowers for the cut flower market. The sprays have stem lengths of about 50 to 56 cm and a vase life of about 8 to 10 days.

Asexual reproduction by budding of the new variety as performed in Watsonville, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depiced in color as nearly true as it is reasonably possible to make the same in a color illustration of this character. Phenotypic expression, including colors, may vary depending upon growing conditions, such as climate, soil, and environmental conditions.

DESCRIPTION OF THE NEW VARIETY

The following is a detailed description of my new variety, with color terminology in accordance with The Royal Horticultural Society Color Chart (R.H.S.C.C.) The terminology used in color description herein refers to plate numbers in the aforementioned color chart. Where general terms such as average, normal, ordinary, medium, etc. are used, the characteristics so described are not considered distinguishing.

Parentage: Seedling.

*Seed parent.*—Unnamed seedling.

*Pollen parent.*—Unnamed seedling.

Class: Floribunda.

The following information is from observations made of specimens grown under glass in Watsonville, Calif. in the month of September.

FLOWER

Blooming habit: Recurrent.

A. Bud:

(1) *Size.*—Small.

(2) *Form.*—Ovoid.

(3) *Color.*—As sepals divide, bud color is near 63A.

(4) *Sepals.*—About 2 to 3 cm, leaf-shaped end with some leafs protruding from sides. Color: Near 146B.

(5) *Peduncle.*—Length: About 4 to 11 cm. Aspect: Smooth. Strength: Erect, sturdy, slender. *Color:* Near 146B.

(6) *Bracts.*—1 to 5 per bud. Color — near 147A. Form — leaf-shaped. Location in relation to flower — about 3 to 6 cm below calyx of bud.

B. Bloom:

(1) *Size.*—About 6 to 7 cm.

(2) *Borne.*—Blooms borne in sprays of about 2 to 8 blooms.

(3) *Form.*—Very nicely imbricated; at maturity petals become slightly ruffled and reflex back.

(4) *Petalage.*—Number of petals under normal conditions — about 37 to 44.

(5) *Color (⅓ to ½ open).*—Outer petals — Top surface near 58C. Undersurface near 58B, Inner petals — Top surface near 58B. Undersurface near 58B. Base of petals — Near 145D. General Tonality from a distance — Deep rose pink.

(6) *Color (fully open).*—Outer petals — Top surface near 63C. Undersurface near 63B. Inner petals — Top surface near 63C. Undersurface near 63B, Base of petals — Near 150D. General tonality from a distance — lighter rose pink than ⅓ to ½ open stage.

(7) *Color change.*—Petals lighten from a deep pink to a lighter pink and develop a magenta tone upon ageing. Petals top surface — lightens. Petal undersurface — lightens. Base of petals — lightens. General tonality at a distance — deep pink.

C. Petals:

(1) *Texture.*—Thick, smooth.

(2) *Appearance.*—Inside velvety; outside slightly satiny.

(3) *Form.*—Elliptic.

(4) *Arrangement.*—Imbricated.

(5) *Petaloids in center.*—About 5 to 8.

(6) *Persistence.*—Petals drop off cleanly.

(7) *Fragrance.*—Mild musk fragrance.

(8) *Lasting quality.*—About 12 to 14 days on plant and 8 to 10 days in vase after cutting.

REPRODUCTIVE ORGANS

A. Stamens, filaments and anthers:

*Arrangement.*—Introse, regularly arranged around styles

*Filaments.*—Color near 145C.

*Anthers.*—Color near 22D.

*Pollen.*—Color near 22D.

B. Styles: Bunched, even, medium length.

*Stigma.*—Color — near 160D.

PLANT

A. Form: Upright, free branching.

B. Growth: Very vigorous.

C. Foliage:

(1) *Size.*—Small.

(2) *Quantity.*—Abundant.

(3) *Color.*—New foliage: Upper side near 147A. Underside near 147B. Old foliage: Upper side near 147A. Underside — near 147B.

(4) *Shape.*—Oval.

(5) *Texture.*—Upper side is smooth, leathery and underside is smooth and slightly leathery.

(6) *Edge.*—Serrated.

(7) *Serration.*—Denticulate.

(8) *Petiole color.*—Top surface — near 137B. Underside near 137C.

(9) *Stipules.*—Adnate.

(10) *Auricle.*—Facing outwards, long.

(11) *Rachis.*—Very small prickles underneath.

(12) *Resistance to disease.*—Very resistant to mildew, rust and blackspot.

D. Wood:

(1) *Old wood.*—Color — near 138B. Bark — smooth.

(2) *Flower stem length from last cutting.*—About 50 cm to about 56 cm.

E. Thorns:

(1) *Thorns.*—Quantity on basal canes — some. Quantity on laterals — very few. Position — irregular.

F. Winter hardiness: Very winter hardy in Holland and Watsonville. Calif.

I claim:

1. A new and distinct variety of rose plant of the floribunda rose class, substantially as shown and described.

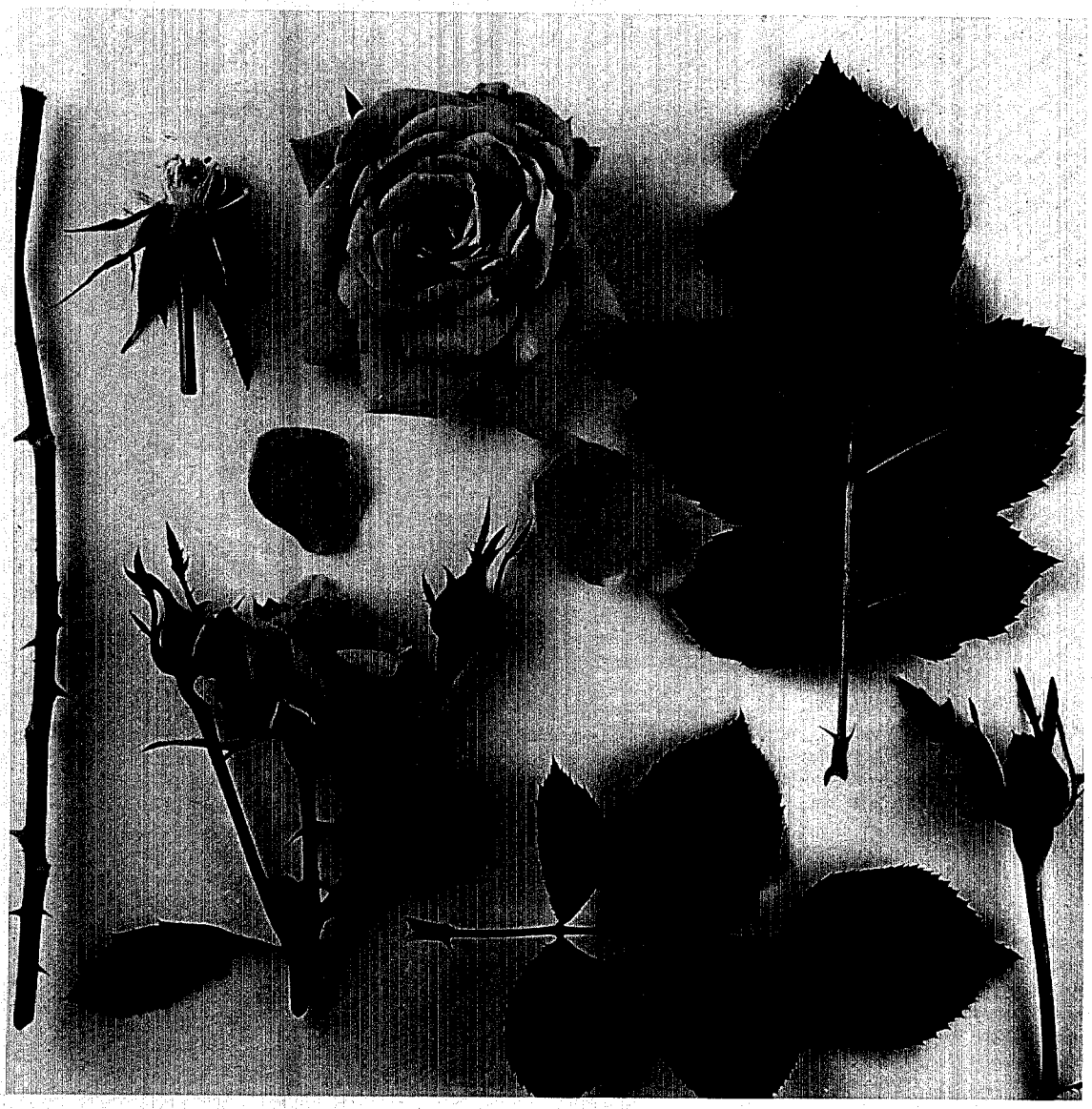

* * * * *